United States Patent
Higgins et al.

(10) Patent No.: US 12,115,085 B2
(45) Date of Patent: Oct. 15, 2024

(54) SURGICAL SYSTEM AND METHOD FOR CHANGING DIMENSION OF HARVESTED TISSUE

(71) Applicant: Arthrex, Inc., Naples, FL (US)

(72) Inventors: Laurence Higgins, Naples, FL (US); Andrew Christian Petry, Naples, FL (US); Reinhold Schmieding, Naples, FL (US); Keith Taylor, Naples, FL (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 405 days.

(21) Appl. No.: 17/498,862

(22) Filed: Oct. 12, 2021

(65) Prior Publication Data
US 2023/0113040 A1     Apr. 13, 2023

(51) Int. Cl.
*A61B 17/00*     (2006.01)
*A61F 2/46*      (2006.01)
(Continued)

(52) U.S. Cl.
CPC ............ *A61F 2/4644* (2013.01); *A61B 17/00* (2013.01); *A61L 27/3691* (2013.01); *B30B 1/20* (2013.01);
(Continued)

(58) Field of Classification Search
CPC .. B30B 1/20; A61F 2/4644; A61F 2002/4649; A61F 2240/002; A61F 2/08;
(Continued)

(56) References Cited

U.S. PATENT DOCUMENTS 2,173,733 A * 9/1939 Seybert ................... A61L 2/06
100/73
4,580,577 A * 4/1986 O'Brien ............. A61B 10/0051
422/430
(Continued)

FOREIGN PATENT DOCUMENTS

CN          202168873 U      3/2012
CN          103767758 B     12/2015
(Continued)

OTHER PUBLICATIONS

English translation of KR-20210082032 A, 11 pages, retrieved in Jul. 2024. (Year: 2024).*

(Continued)

*Primary Examiner* — Jimmy T Nguyen
(74) *Attorney, Agent, or Firm* — Carlson, Gaskey & Olds, P.C.

(57) ABSTRACT

This disclosure details a surgical system and method for changing one or more dimensions of harvested tissue, such an autograft, which is harvested from one location in a patient's body and used for a surgical repair or reconstruction procedure in another location in the patient's body. An example surgical system includes a first press component defining a cavity configured to receive harvested tissue, and a second press component including a projection insertable into the cavity. Further, at least one of the first and second press components are made of a transparent or semi-transparent material such that when harvested tissue is in the cavity and when the projection is inserted into the cavity, the harvested tissue is visible through at least one of the first and second press components.

5 Claims, 4 Drawing Sheets

(51) Int. Cl.
*A61L 27/36* (2006.01)
*B30B 1/20* (2006.01)

(52) U.S. Cl.
CPC .............. *A61B 2017/00969* (2013.01); *A61F 2002/4649* (2013.01)

(58) Field of Classification Search
CPC .................. A61B 17/00; A61B 17/322; A61B 2017/00907; A61B 2017/3225; A61L 27/3691
See application file for complete search history.

(56) References Cited

U.S. PATENT DOCUMENTS

| | | | |
|---|---|---|---|
| 5,329,846 | A | 7/1994 | Bonutti |
| 5,467,699 | A * | 11/1995 | Laib ........................ A47J 19/06 |
| | | | 100/234 |
| 5,545,222 | A | 8/1996 | Bonutti |
| 6,309,405 | B1 | 10/2001 | Bonutti |
| 6,503,277 | B2 | 1/2003 | Bonutti |
| 6,630,153 | B2 | 10/2003 | Long et al. |
| 6,652,260 | B2 | 11/2003 | Nelson et al. |
| 6,776,938 | B2 | 8/2004 | Bonutti |
| 6,860,904 | B2 | 3/2005 | Bonutti |
| 7,189,245 | B2 | 3/2007 | Kaplan |
| 7,462,200 | B2 | 12/2008 | Bonutti |
| 8,617,181 | B2 | 12/2013 | Sabir et al. |
| 8,974,535 | B2 | 3/2015 | Antonyshyn et al. |
| 9,615,922 | B2 | 4/2017 | Munnelly et al. |
| 9,616,152 | B2 | 4/2017 | Samaniego et al. |
| 9,752,112 | B2 | 9/2017 | Watanabe et al. |
| 10,717,249 | B1 * | 7/2020 | Kim ........................ A23P 30/10 |
| 2002/0025358 | A1 | 2/2002 | Nelson et al. |
| 2002/0040246 | A1 | 4/2002 | Bonutti |
| 2002/0106625 | A1 | 8/2002 | Hung et al. |
| 2004/0019132 | A1 | 1/2004 | Long et al. |
| 2012/0277152 | A1 | 11/2012 | Ringeisen et al. |
| 2012/0303058 | A1 | 11/2012 | Huttunen et al. |
| 2013/0134632 | A1 | 5/2013 | Snedeker et al. |
| 2017/0128215 | A1 | 5/2017 | Denham |
| 2017/0273795 | A1 | 9/2017 | Neichel et al. |
| 2021/0236302 | A1 * | 8/2021 | Kim ........................ A61F 2/4644 |

FOREIGN PATENT DOCUMENTS

| | | | | |
|---|---|---|---|---|
| EP | 2528543 | B1 | 10/2016 | |
| KR | 200432065 | Y1 * | 11/2006 | .............. A47J 43/07 |
| KR | 20210082032 | A * | 7/2021 | .............. B30B 11/02 |
| WO | 2020050514 | A1 | 3/2020 | |

OTHER PUBLICATIONS

English translation of KR 1553193 B1, 3 pages, retrieved in Jul. 2024. (Year: 2024).*
English translation of KR200432065Y1, 6 pages, retrieved in Aug. 2024. (Year: 2024).*
McKesson "Paparella tissue press disposable, ENT specialty" https://mms.mckesson.com/product/922115/V-Mueller-AU13855. 2021.
Arthrex "Univers Revers Modular Glenoid System—Surgical technique". pp 1-28. 2021.
Colbath G, Murray A, Siatkowski S, Pate T, Krussig M, Pill S, Hawkins R, Tokish J, Mercuri J, Autograft long head biceps tendon can be used as a scaffold for biologically augmenting rotator cuff repairs., Arthroscopy: The Journal of Arthroscopic and Related Surgery (2021), doi: https://doi.org/10.1016/j.arthro.2021.05.064.
International Search Report and Written Opinion for PCTIUS2022I44197 dated Jan. 3, 2023.

* cited by examiner

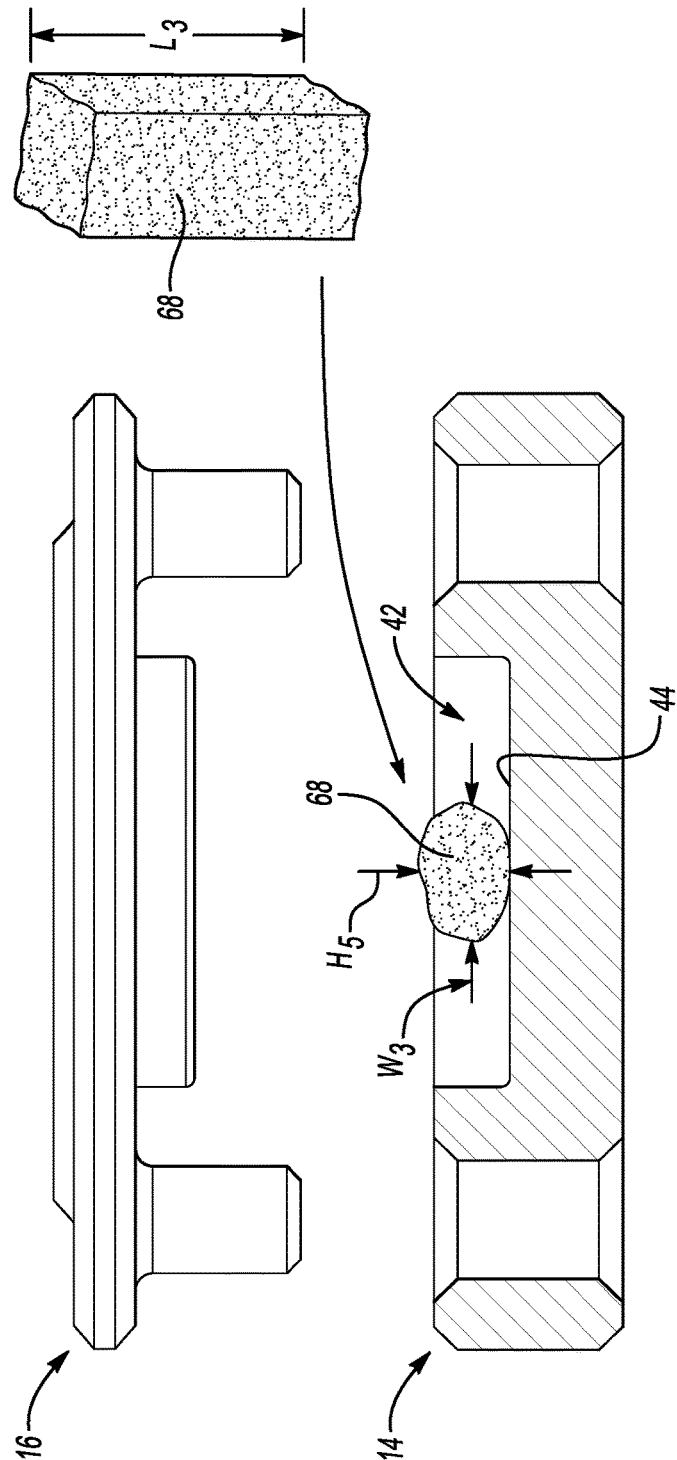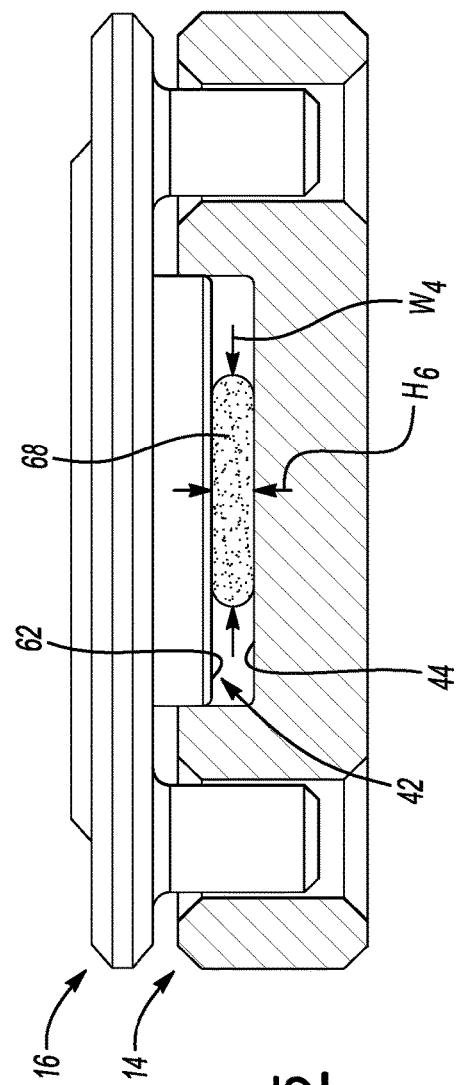

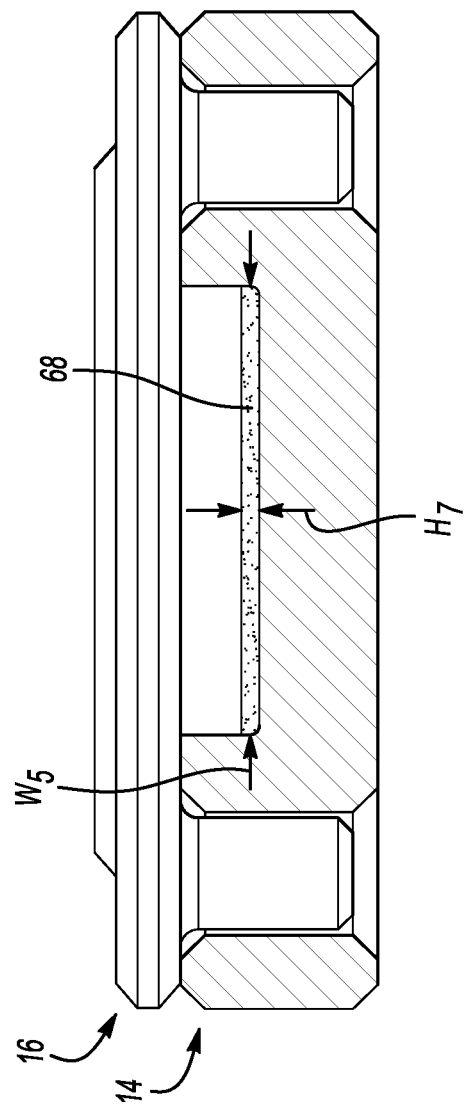
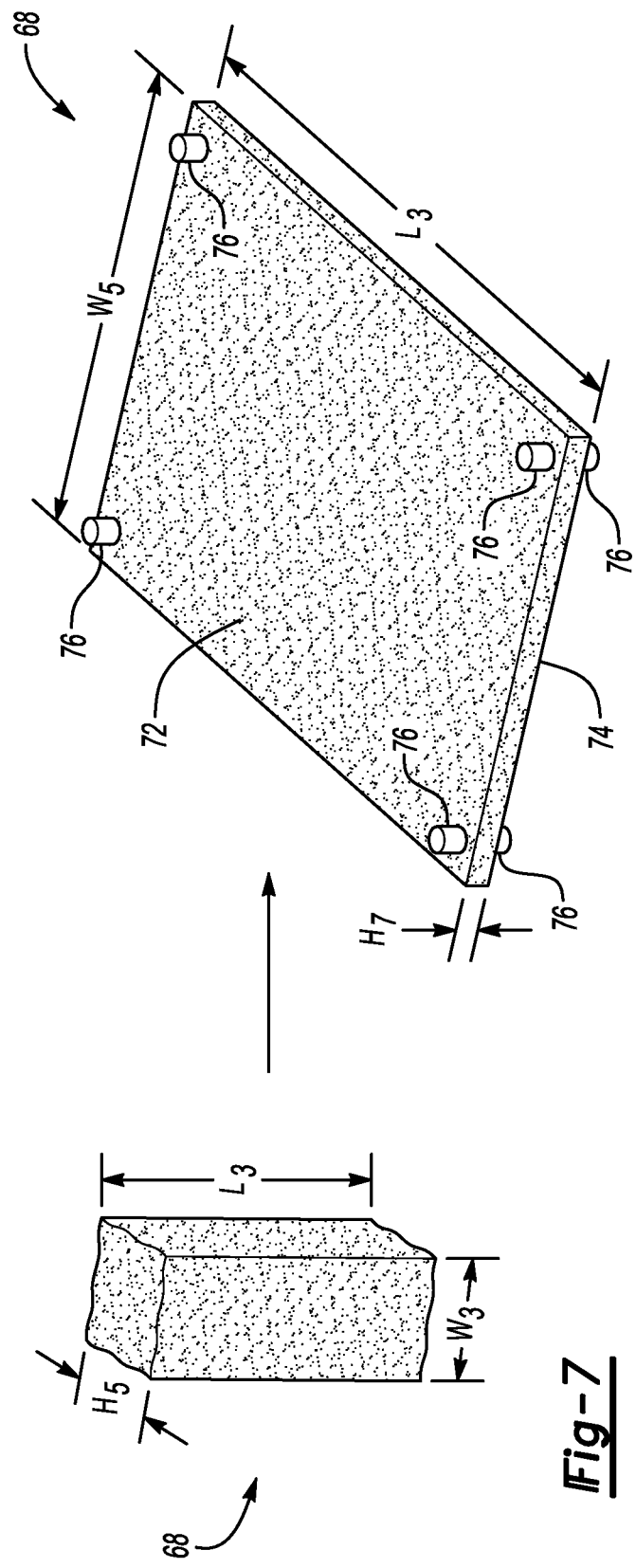

SURGICAL SYSTEM AND METHOD FOR CHANGING DIMENSION OF HARVESTED TISSUE

BACKGROUND

To re-establish stability within a shoulder joint after injury, for example, autograft tissue can be employed to span the humerus and the glenoid cavity of the scapula and repair the rotator cuff. Allograft tissue is an alternate option.

SUMMARY

This disclosure details a surgical system and method for changing one or more dimensions of harvested tissue, such as autograft, which is harvested from one location in a patient's body and used for a surgical repair or reconstruction procedure in another location in the patient's body. This disclosure also relates to the method of changing one or more dimensions of the harvested tissue, as well as the method of performing a surgical procedure including one or more steps associated with changing the dimension(s) of the harvested tissue.

Among other benefits, the disclosed system and method permit use of autograft tissue for joint repair and reconstruction procedures without requiring a relatively large piece of tissue to be harvested from a donor site. Further, the disclosed system and method permit a user to view the harvested tissue as the dimension(s) of the harvested tissue are changed, which permits the user to readily determine when a desired dimension(s) is reached. Further still, the system and method result in a piece of harvested tissue with features configured to resist suture pull-out.

A system configured to change a dimension of harvested tissue according to an exemplary aspect of the present disclosure includes, among other things, a first press component defining a cavity configured to receive harvested tissue, and a second press component including a projection insertable into the cavity. Further, at least one of the first and second press components are made of a transparent or semi-transparent material such that when harvested tissue is in the cavity and when the projection is inserted into the cavity, the harvested tissue is visible through at least one of the first and second press components.

A surgical method according to an exemplary aspect of the present disclosure includes, among other things, placing harvested tissue into a cavity of a first press component, changing a dimension of the harvested tissue by inserting a projection of a second press component into the cavity of the first press component, and viewing the harvested tissue through at least one of the first press component and the second press component during the changing step. Further, the at least one of the first and second press components is made of a transparent or semi-transparent material.

BRIEF DESCRIPTION OF THE DRAWINGS

FIG. 4 is a view of the first press component spaced-apart from the second press component such that a piece of harvested tissue can be placed into the cavity of the first press component. In FIG. 4, the first press component and the piece of harvested tissue are shown in cross-section.

FIG. 5 is a view similar to FIG. 4, but with the projection of the second press component being partially inserted into the cavity such that the piece of harvested tissue is compressed relative to its state in FIG. 4.

FIG. 6 is another view similar to FIGS. 4 and 5, but with the second press component being inserted further into the cavity relative to the position of the second press component in FIG. 5. In FIG. 6, the piece of harvested tissue is further compressed relative to its state in FIG. 5.

FIG. 7 illustrates an example piece of harvested tissue after harvesting on the left-hand side, and, on the right-hand side, illustrates the example piece of harvested tissue after use of the press.

DETAILED DESCRIPTION

Figure 1:
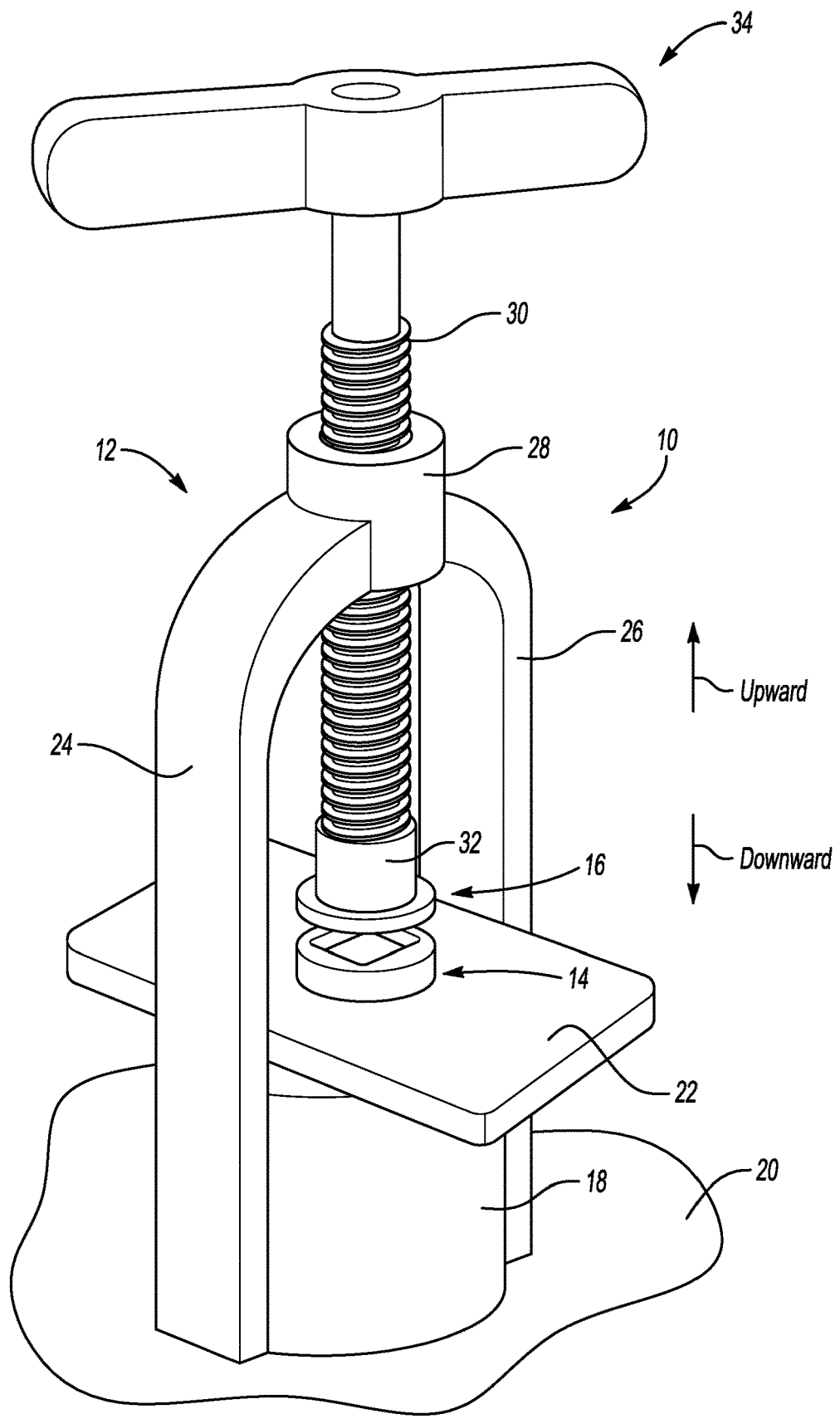
FIG. 1 is a perspective view of an example surgical system.

This disclosure details a surgical system and method for changing one or more dimensions of harvested tissue. With reference to the drawings, FIG. 1 illustrates an example surgical system 10 ("system 10"). As shown in FIG. 1, the system 10 includes a press 12, a first press component 14, and a second press component 16. The press 12, in this example, is manually operated and is configured to move the first and second press components 14, 16 relative to one another to compress, and thereby flatten and change one or more dimensions of, a harvested piece of tissue. While the press 12 is manually operated in this example, one or more components of the press 12 could be controlled using an electromechanical and/or hydraulic device, such as an actuator. Further, while one example press 12 is shown in FIG. 1, it should be understood that this disclosure extends to other devices configured to apply forces resulting in relative movement of the first and second press components 14, 16, including clamps, vises, levers, etc.

In this example, the press 12 includes a stand 18 configured to rest on a worktop 20 or other surface, such as a table. The press 12 also includes a base 22 mounted above the stand 18. With reference to directional terms, the "upward" and "downward" directions are labeled in FIG. 1 and are used with reference to the normal operating orientation of the press 12. The first press component 14 is mounted to the base 22. In this example, the first press component 14 and base 22 are configured to remain stationary during use of the press 12.

The press 12 further includes a pair of support arms 24, 26 projecting from opposite sides of the stand 18 and converging on a nut 28 spaced upward of the base 22. The nut 28 is configured to remain stationary during use of the press 12. The nut 28 includes a threaded through-bore which receives a shaft 30. The shaft 30 is at least partially threaded, and the threads of the shaft 30 cooperate with threads of the nut 28 such that rotation of the shaft 30 results in movement of the shaft 30 in either the upward or downward direction relative to the nut 28 depending on the direction of rotation.

Below the nut 28, the shaft 30 is connected to the second press component 16 via a connector 32, which is mounted adjacent an end of the shaft 30. The connector 32 is configured to transmit vertical movement of the shaft 30 to the second press component 16 without transmitting rotational movement of the shaft 30 to the second press component 16. The connector 32 can be integrally formed with the second press component 16. Above the nut 28, the shaft 30 is connected to a handle 34. The handle 34 permits a user, such as a surgeon or surgical assistant, to apply a rotational force to the shaft 30 via the handle 34. Ultimately, the user is able to selectively raise and lower the second press component 16 relative to the first press component 14 by rotating the handle 34.

The first and second press components 14, 16 may be referred to as female and male components, respectively. In this example, the first press component 14 defines a cavity, and thus the first press component 14 may alternatively referred to as a cavity. Further, the second press component 16 includes a projection configured for insertion into the cavity, and thus the second press component 16 may alternatively be referred to as a core. In this regard, the term "component" as used in the context of the first and second press components 14, 16 is not intended to be a nonce term or placeholder serving as a substitute for "means."

Figure 2:
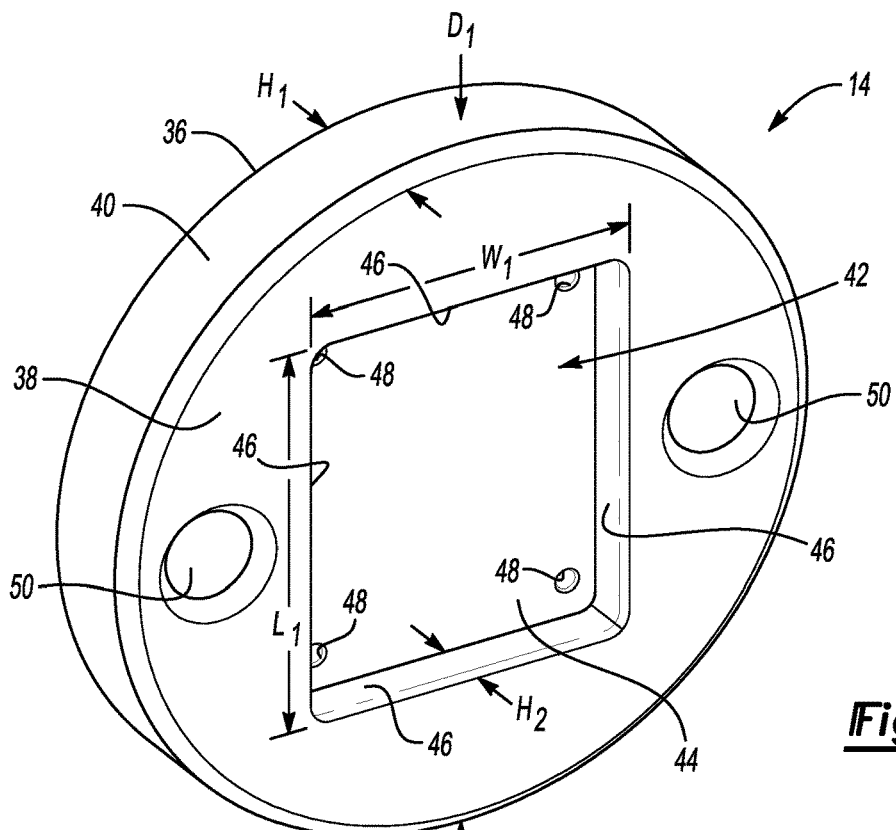
FIG. 2 is a top-perspective view of an example first press component, which defines a cavity.

FIG. 2 illustrates additional detail of the first press component 14. The first press component 14 exhibits a height $H_1$ between a bottom surface 36 and a top surface 38. The bottom surface 36 is configured to rest upon, and be fixed to, the base 22. The bottom surface 36 may include one or more attachment features configured to facilitate an attachment of the first press component 14 to the base 22. In this example, the first press component 14 exhibits a circular perimeter 40 defined by a diameter $D_1$. The perimeter 40 could exhibit other shapes, however.

A cavity 42 is defined by the first press component 14. Specifically, in this example, the cavity 42 is recessed downward, toward the bottom surface 36, from the top surface 38. A majority of a bottom surface of the cavity 42 is defined and bound by a main upward-facing forming surface 44. The main upward-facing forming surface 44 is recessed by a height $H_2$, which is less than $H_1$, from the top surface 38. The cavity 42 is bound by four walls 46, in this example, which provide the cavity 42 with a rectangular shape having a length $L_1$ greater than a width $W_1$. Other cavity shapes come within the scope of this disclosure. The walls 46 exhibit the height $H_2$ and are oriented at 90° angles relative to adjacent walls 46. Further, there are rounded corners to provide smooth transitions between the walls 46.

In this example, the first press component 14 further includes a plurality of forming holes 48 configured to form raised areas in a piece of harvested tissue. The forming holes 48 extend downward from the main upward-facing forming surface 44. The forming holes 48 are arranged adjacent the perimeter of the main upward-facing forming surface 44, and specifically adjacent corners of the cavity 42, in this example. In particular, there are four forming holes 48 in this example, and the forming holes 48 are arranged adjacent intersections of the four walls 46. The forming holes 48 are spaced inward, toward a center of the main upward-facing forming surface 44 such that an amount of space, which is relatively small, is present between the forming holes 48 and the walls 46. In this example, the forming holes 48 are through holes and extend from the main upward-facing forming surface 44 through to the bottom surface 36. In other examples, the forming holes 48 are recessed downward from the main upward-facing forming surface 44 but do not extend through to the bottom surface 36.

The first press component 14 includes two guide openings 50 on opposite sides of the cavity 42. The guide openings 50 are through holes extending from the top surface 38 through to the bottom surface 36. The guide openings 50 are configured to receive guide pins of the second press component 16 to facilitate alignment of the first and second press components 14, 16 during use of the press 12.

Figure 3:
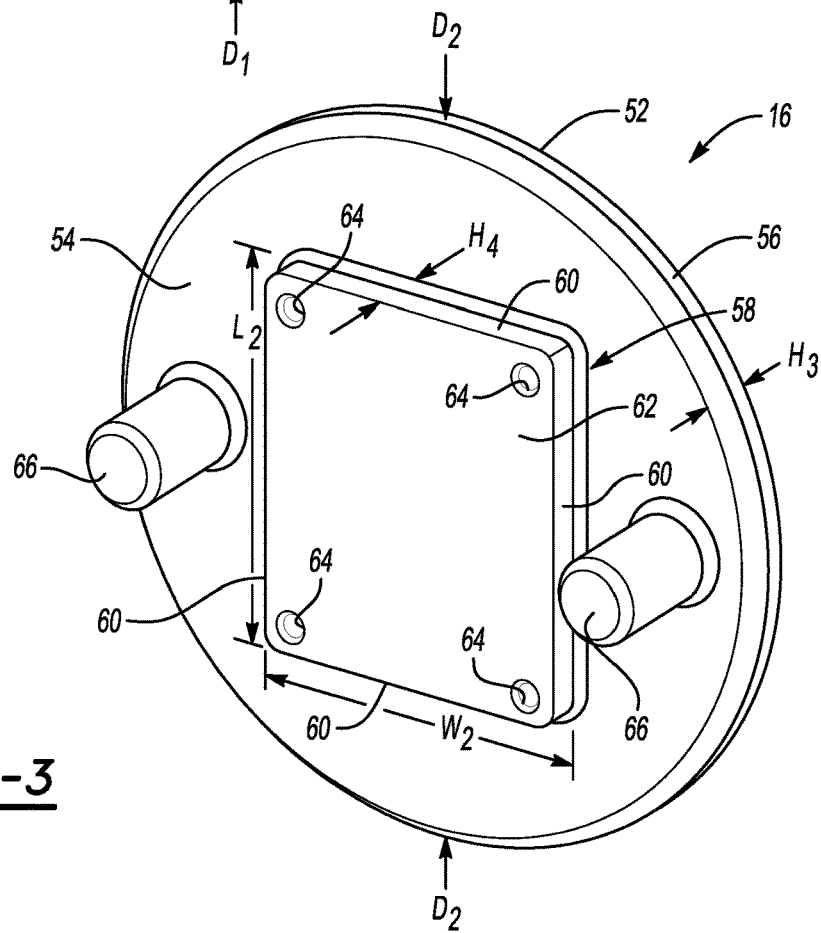
FIG. 3 is a bottom-perspective view of an example second press component, which includes a projection configured for insertion into the cavity.

Additional detail of the second press component 16 is illustrated in FIG. 3. The second press component 16 exhibits a height $H_3$ between a top surface 52 and a bottom surface 54. The top surface 52 is configured to attach to the connector 32. The top surface 52 may include one or more attachment features configured to facilitate attachment to the connector 32. In this example, the second press component 16 exhibits a circular perimeter 56 defined by a diameter $D_2$, which is substantially equal to $D_1$. The perimeter 56 could exhibit other shapes, however.

The second press component 16, in this example, includes a projection 58 projecting downward from the bottom surface 54. The projection 58 is bound by four walls 60, each of which exhibit a height $H_4$, and which provide the projection 58 with a rectangular shape exhibiting a length $L_2$ and a width $W_2$. The walls 60 are arranged at 90° relative to one another, with rounded corners, in a similar manner as the walls 46. In this example, the height $H_4$ is substantially equal to the height $H_2$. In a particular example, the height $H_4$ is slightly greater than the height $H_2$. Further, in this example, the length $L_2$ and width $W_2$ are substantially equal to, but slightly less than, the corresponding length $L_1$ and width $W_1$ of the cavity 42 such that the projection 58 fits into the cavity 42 to provide a sliding fit between the cavity 42 and projection 58. The projection 58 exhibits a main downward-facing forming surface 62, which is spaced-apart from the bottom surface 54 by height $H_4$, and exhibits the length $L_2$ and the width $W_2$.

In this example, the second press component 16 further includes a plurality of forming holes 64 configured to form raised features in a piece of harvested tissue. When the second press component 16 is mounted to the press 12, the forming holes 64 are aligned with and vertically overlap corresponding forming holes 48 in the first press component 14. The forming holes 64 are recessed from the main downward-facing forming surface 62 and specifically extend upward from the main downward-facing forming surface 62. The forming holes 64 are arranged adjacent corners of the main downward-facing forming surface 62, in this example. Specifically, there are four forming holes 64 in this example, and the forming holes 64 are arranged adjacent an outer perimeter of the main downward-facing forming surface 62, namely adjacent intersections of the four walls 60. The forming holes 64 are spaced inward, toward a center of the main downward-facing forming surface 62 such an amount of space, which is relatively small, is present between the forming holes 64 and the walls 60. In this example, the forming holes 64 are through holes and extend from the main downward-facing forming surface 62 through to the top surface 52. In other examples, the forming holes 64 are recessed upward from the main downward-facing forming surface 62 but do not extend through to the top surface 52.

In order to facilitate alignment of the first and second press components 14, 16, and to further facilitate a sliding fit between the cavity 42 and the projection 58, the second press component 16 includes guide pins 66 on opposite sides of the projection 58. The guide pins 66 are configured to align with and be received in the guide openings 50 of the first press component 14. The guide openings 50 and guide pins 66 are dimensioned so as to permit a sliding fit between the guide openings 50 and guide pins 66.

While four forming holes 48, 64 are provided in each of the first and second press components 14, 16, it should be understood that this disclosure extends to embodiments with fewer or additional forming holes. For instance, forming holes could be provided about the entire perimeter of the cavity 42 and the projection 58 such that there are greater than four forming holes in each of the first and second press components 14, 16.

In this disclosure, at least one of the first press component 14 and the second press component 16 are made of at least a semi-transparent material such that a harvested piece of tissue can be viewed through the first press component 14 and/or the second press component 16 while the press 12 is in use. In a further aspect of this disclosure, at least one of the first press component 14 and the second press component 16 is formed of a transparent material. An example transparent material is a clear polycarbonate material. Other transparent materials come within the scope of this disclosure. In a specific example, at least the second press component 16 is made of transparent material. In an even more specific example, both the first and second press components 14, 16 are made of transparent material. By providing at least one of the first and second press components 14, 16 of at least semi-transparent, if not fully transparent material, the harvested tissue is visible through at least one of the first and second press components 14, 16. When both the first and second press components 14, 16 are made of semi-transparent or fully transparent material, the vertical dimension, or height, of the piece of harvested tissue may be more readily visible. Regardless, a user of the press 12 can monitor the reaction of the piece of harvested tissue as compressive forces are applied to the piece of harvested tissue to determine if one or more dimensions of the harvested tissue have been changed as desired such that the user can cease use of the press 12. In other words, the user can determine whether the press 12 is applying an appropriate pressure to the harvested tissue for an appropriate time to achieve the desired change in dimension(s) of the harvested tissue.

An example method of use will now be described relative to FIGS. 4-7. A surgeon may perform the method either partially or entirely. One or more steps of the method may be performed by another, such as a surgical assistant. The method may be performed either partially or entirely during an arthroscopic surgical procedure.

Initially, tissue is harvested from a first location in a body of a patient. In an example, the first location is one of the latissimus dorsi, pectoralis major, and fascia lata. This disclosure extends to other harvesting locations. Following harvesting, the example piece of harvested tissue 68, as shown in FIG. 4 and the left-hand side of FIG. 7, exhibits a length $L_3$, a width $W_3$, and a height $H_5$. While shown as a substantial rectangular cuboid, in another example the harvested tissue 68 is substantially cylindrical.

After harvesting, the harvested tissue 68 is situated relative to the press 12 such that the user can change at least one dimension of the harvested tissue 68 such that the harvested tissue 68 is suitable for implantation in a second location in the body of the patient. In an example, the second location is adjacent a rotator cuff or another location. In this regard, the harvested tissue 68 is an autograft harvested from one location of a patient's body and used to repair or reconstruct a joint in another location of the patient's body. In a particular example, the harvested tissue 68 is used to provide a partial or full replacement for a torn rotator cuff. This disclosure is not limited to use in rotator cuff repairs/reconstructions, however, and extends to the harvested tissue 68 being used in other repair or reconstruction techniques, including techniques involving repair or reconstruction of the hand, wrist, toe, Achilles tendon, Peroneal/Tibial tendon, among others. As another example, the harvested tissue 68 may be used in a superior capsular reinforcement technique.

As shown in FIG. 4, the harvested tissue 68 is placed in the cavity 42 of the first press component 14. In FIG. 4, the user has rotated the handle 34 such that the second press component 16 is spaced-apart vertically upward of the first press component 14 to permit placement of the harvested tissue 68 into the cavity 42. The first press component 14 and the harvested tissue 68 are shown in cross-section. The harvested tissue 68 in this example exhibits a length $L_5$ substantially equal to the length $L_1$ of the cavity. In FIG. 4, the user has placed the harvested tissue 68 such that it is arranged substantially centrally, relative to the width dimension $W_1$, on the main upward-facing forming surface 44.

Once the harvested tissue 68 is arranged in the cavity 42, the user begins rotating the handle 34 to lower the second press component 16 such that the main downward-facing forming surface 62 comes into contact with the harvested tissue 68 and is inserted into the cavity 42, as shown in FIG. 5. The compressive forces of the press 12 cause the harvested tissue 68 to become compressed, and thereby become flattened, between the main upward-facing forming surface 48 and the main downward-facing forming surface 62. As shown in FIG. 5, the harvested tissue 68 exhibits a width $W_4$ greater than the width $W_3$ and a height $H_6$ less than the height $H_5$. The user is able to view the changed dimensions of the harvested tissue 68 through one or both of the first and second press components 14, 16, which again may be semi-transparent or fully transparent.

If the user desires a greater width and lesser height of the harvested tissue 68, then the user continues rotating the handle 34 to lower the second press component 16 further, applying even greater compressive forces, until the harvested tissue 68 reaches the state of FIG. 6, which illustrates the harvested tissue 68 exhibiting a width $W_5$ and a height $H_7$. In FIG. 6, the width $W_5$ is greater than the width $W_4$ and is substantially equal to the width $W_1$, and the height $H_7$ is less than the height $H_6$. Again, the user is able to determine when the harvested tissue 68 reaches this state because the user can view the harvested tissue 68 through one or both of the first and second press components 14, 16. Once the harvested tissue 68 reaches the state of FIG. 6, the user may hold the second press component 16 in position for a period of time and then retract the second press component 16 and retrieve the harvested tissue 68, which exhibits changed dimensions relative to its state in FIG. 4.

The right-hand side of FIG. 7 is representative of the harvested tissue 68 following the steps of FIGS. 4-6. In FIG. 7, the harvested tissue exhibits a length $L_3$, which is substantially unchanged relative to FIG. 4, a width $W_5$, which is greater than the width $W_3$ of FIG. 4 and which is substantially equal to the width $W_1$ of the cavity 42, and a height $H_7$. More particularly, the harvested tissue 68 exhibits the height $H_7$ across a majority of the surface area of main upper and lower surfaces 72, 74 of the harvested tissue 68, other than portions of the harvested tissue 68 corresponding to locations of the forming holes 48, 64. At those locations, the harvested tissue 68 exhibits raised areas 76 projecting away from the main upper and lower surfaces 72, 74 of the harvested tissue 68. Specifically, as the second press component 16 is lowered, the harvested tissue 68 is pressed into the forming holes 48, 64, such that four raised areas 76 project from the main upper surface 72 and four raised areas 76 project downward from the main lower surface 74. The raised areas 76 are substantially cylindrical and exhibit a shape corresponding to the shape of the forming holes 48, 64. The harvested tissue 68 exhibits a greater height than height $H_7$ at the locations of the raised areas 76. As such, when implanting the harvested tissue 68, the locations corresponding to the raised areas 76 may be suited for threading of suture as the increased height at the raised areas 76 may make these locations better suited to resist suture pull-out. In this regard, the method includes placing suture through at least one of the raised areas 76 during implantation of the harvested tissue 68.

The main upward- and downward-facing forming surfaces 44, 62 are parallel to one another when the first and second press components 14, 16 are mounted in the press 12. As such, with reference to the harvested tissue 68 on the left-hand side of FIG. 7, the main upward- and downward-facing forming surfaces 44, 62 are configured to provide the harvested tissue 68 with main upper and lower surfaces 72, 74 which are substantially parallel to one another. The main upward- and downward-facing forming surfaces 44, 62 are configured to directly contact, and in turn form, the harvested tissue 68 during use of the press 12. Further, the forming holes 48, 64 are configured to directly contact, and in turn form, the harvested tissue 68 as well.

It should be understood that directional terms such as top, bottom, upward, downward, etc., are used herein consistent with their art-accepted meaning and with reference to the normal operational orientation of the relevant components. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A system configured to change a dimension of harvested tissue, comprising:

a first press component defining a cavity configured to receive harvested tissue;

a second press component including a projection insertable into the cavity, wherein at least one of the first and second press components is made of a transparent or semi-transparent material such that when harvested tissue is in the cavity and when the projection is inserted into the cavity, the harvested tissue is visible through at least one of the first and second press components;

wherein the first press component is a bottom press component, wherein the cavity is bound in part by a main upward-facing forming surface, wherein the first press component includes a plurality of forming holes recessed downward from the main upward-facing forming surface, wherein the second press component is a top press component, wherein the projection includes a main downward-facing forming surface, and wherein the second press component includes a plurality of forming holes recessed upward from the main downward-facing forming surface.

2. The system as recited in claim 1, wherein the plurality of forming holes of the first press component are adjacent an outer perimeter of the main upward-facing forming surface.

3. The system as recited in claim 1, wherein the plurality of forming holes of the first press component extend through an entirety of a height dimension of the first press component.

4. The system as recited in claim 1, wherein the plurality of forming holes of the second press component are adjacent an outer perimeter of the main downward-facing forming surface.

5. The system as recited in claim 4, wherein the plurality of forming holes of the second press component extend through an entirety of a height dimension of the second press component.

* * * * *